(12) United States Patent
Xu et al.

(10) Patent No.: US 10,426,863 B2
(45) Date of Patent: Oct. 1, 2019

(54) LIQUID SPRAY DEVICE WITH CONCEALED ELECTRIC CONDUCTIVE STRUCTURE

(71) Applicant: Vida International Inc., Taipei (TW)

(72) Inventors: Zhi-Kai Xu, Ontario, CA (US);
Bing-Xin Zhu, Taipei Hsien (TW)

(73) Assignee: Vida International Inc., Taipei (TW)

(*) Notice: Subject to any disclaimer, the term of this patent is extended or adjusted under 35 U.S.C. 154(b) by 0 days.

(21) Appl. No.: 15/834,825

(22) Filed: Dec. 7, 2017

(65) Prior Publication Data
US 2018/0161473 A1   Jun. 14, 2018

(30) Foreign Application Priority Data

Dec. 8, 2016  (TW) .............................. 105218712 U

(51) Int. Cl.
*A61L 9/14* (2006.01)
*B05B 17/06* (2006.01)

(52) U.S. Cl.
CPC ............ *A61L 9/14* (2013.01); *B05B 17/0607* (2013.01); *A61L 2209/11* (2013.01); *A61L 2209/13* (2013.01); *A61L 2209/132* (2013.01); *A61L 2209/134* (2013.01)

(58) Field of Classification Search
CPC .... A61L 9/14; A61L 2209/11; A61L 2209/13; B05B 17/04; B05B 17/06; B05B 17/0607
See application file for complete search history.

(56) References Cited

U.S. PATENT DOCUMENTS

| | | | | |
|---|---|---|---|---|
| 9,016,595 | B2* | 4/2015 | Akitsu ................ | B05B 17/0646 239/102.1 |
| 9,149,553 | B2* | 10/2015 | Akitsu ................ | B05B 17/0684 |
| 2007/0235555 | A1* | 10/2007 | Helf ...................... | A01M 1/205 239/102.2 |

* cited by examiner

*Primary Examiner* — Darren W Gorman
(74) *Attorney, Agent, or Firm* — Alan G. Towner; Leech Tishman Fuscaldo & Lampl

(57) ABSTRACT

A liquid spray device with concealed electric conductive structure is used for atomizing the liquid stored therein and then spraying the atomized liquid. The device comprises a base, a controller on a front side of the base, a liquid storage container that can be separately arranged above or below the controller, a sprayer including a bracket movably pivoted on the controller, a vibrator arranged on the bracket, a liquid sucking outlet that allows the vibrator to abut against the liquid storage container, and a housing covering the base. A conductive pivoting structure is provided between the controller and the bracket, the bracket is provided with a wire recess, and a wire is provided within the wire recess, which allows one end of the wire to be electrically connected to the conductive pivoting structure, while the other end thereof is electrically connected to the vibrator. In this way, the wire is concealed within the bracket, and the electric conductive structure has dual functions of pivoting and conducting.

8 Claims, 4 Drawing Sheets

LIQUID SPRAY DEVICE WITH CONCEALED ELECTRIC CONDUCTIVE STRUCTURE

FIELD OF THE INVENTION

The present utility model relates to a liquid spray device, and more specifically to an improved liquid spray device that can atomize and then spray the liquid.

BACKGROUND

In reference to FIG. 1, a conventional liquid spray device is typically used to atomize and then spray a liquid; in particular a wall mounted liquid spray device that is used to atomize and then spray an air refresher. It typically comprises a base 10, a control means 20, a liquid storage unit 30, a spray unit 40 and a housing 50, etc., in which the base 10 is usually a vertical base, and the control means 20 is fixed on the d front side of the base, the control means 20 is provided with a control unit including circuit board, microprocessor and the like, which function to control the duration and times of spray. The liquid storage unit 30 can be arranged separately above or below the control means 20, which is used to store the liquid of air refresher, and the like. In addition, one end of the liquid storage unit is provided with a sucking outlet 301. The spray unit 40 comprises a bracket 401, a vibrator 402 and a wire 403, wherein the bracket 401 is pivoted on two sides of the control means 20, the vibrator 402 may abut against the sucking outlet 301 of the liquid storage unit 30, and the wire 403 is electrically connected to the vibrator 402 and the control means 20. The housing 50 is pivoted to the base 10 to cover the control means 20, the liquid storage unit 30 and the spray unit 40. The front side of the housing is provided with a pair of spray opening 502 corresponding to the vibrator 402. In this way, by way of setting the control means 20, a control signal and electric power can be sent from the control means 20 to the vibrator 402 via the wire 403, which further drive the vibrator 402 to generate a high frequency vibration to atomize the liquid at the sucking outlet 301; and the atomized liquid is next sprayed out via the spray opening 501 of the housing 50.

However, in the foregoing structure, the vibrator 402 of the spray unit 40 is connected to the control means 20 via the wire 403. Hence, the wire 403 is exposed between the control means 20 and the bracket 401. On the other hand, the liquid storage unit 30 is a disposable part, when the liquid therein runs out; the liquid storage unit will be replaced by a new liquid storage unit 30 manually. Accordingly, when the housing 50 is opened for replacement, the wire 403 will be completely exposed which increases the risk of accidentally touching the wire or break the wire. In addition, due to the exposed wire therein, its configuration is unnecessarily complex. Hence, hiding the wire 403 and at the same time retaining its electric connection with the control means 20 become the key technical problems to be overcome in the present utility model.

SUMMARY OF THE INVENTION

The object of the present utility model is to provide a liquid spray device with concealed electric conductive structure, wherein the structure pivoting bracket further has the function of electric conduction, so as to achieve the objects of concealing the wire, preventing the wire from being torn off, and more easily assembling the bracket.

In order to achieve the foregoing objects, the present utility model provides a liquid spray device with concealed electric conductive structure, which is used for atomizing and then spraying the liquid stored therein. One of its preferred technical solutions is as follows: the liquid spray device with a concealed electric conductive structure comprises: a base, a control means, wherein the control means is arranged on a front side of the base, a liquid storage means, wherein the liquid storage means is separately arranged above or below the control means, and is provided with a liquid sucking outlet, a spray unit, wherein the spray unit comprises a bracket, a vibrator arranged on the bracket, the bracket is movably pivoted on the control means, and the vibrator abuts against the liquid sucking outlet of the liquid storage means via the movement of the bracket, and a housing, wherein the housing is separately connected to the base to cover the control means and the spray unit, a spray opening is provided at a location corresponding to the vibrator, the device is characterized in that a conductive pivoting structure is provided between the control means and the bracket, the bracket is provided with a wire recess, and a wire is arranged within the wire recess, one end of the wire is electrically connected to the conductive pivoting structure, and the other end of the wire is electrically connected to the vibrator.

In the liquid spray device with a concealed electric conductive structure mentioned above, the conductive pivoting structure comprises a pivoting part provided on the bracket, the pivoting part comprises a pivot hole, a conductive element is provided in the pivot hole, one end of the wire is electrically connected to the conductive element, the other end of the wire is electrically connected to the vibrator, one rod shaped metal terminal is provided on one side of the control means, one outer end of the metal terminal extends into the pivot hole of the pivoting part on the bracket, the outer end of the metal terminal contacts the conductive element, and one inner end of the metal terminal extends into the control means and conductively connects to a control unit in the control means.

In the liquid spray device with a concealed electric conductive structure mentioned above, the bracket comprises a cross bar and two vertical bars connected to two ends of the cross bar, one sides of the cross bar and the vertical bars are provided with the wire recess, the vibrator is arranged on the cross bar, and the pivoting part is arranged on one end of the vertical bar.

In the liquid spray device with a concealed electric conductive structure mentioned above, the conductive element is a metal sheet.

In the liquid spray device with a concealed electric conductive structure mentioned above, the metal terminal is a cylinder, and the metal terminal is movably arranged to pass through one side of the control means.

In the liquid spray device with a concealed electric conductive structure mentioned above, the conductive pivoting structure further comprises an elastic element, one end of the elastic element abuts against the metal terminal, and the other end of the elastic element abuts against the control means.

In the liquid spray device with a concealed electric conductive structure mentioned above, the control means comprises a case, one side of the case is provided with an accommodating hole, the metal terminal is movably arranged to pass through the accommodating hole, the elastic element is a spiral spring set outside of the metal terminal, one end of the spiral spring abuts against a convex ring portion of the metal terminal, and the other end of the spiral spring abuts in the accommodating hole.

In the liquid spray device with a concealed electric conductive structure mentioned above, the outer end of the metal terminal protrudes from the accommodating hole.

In the liquid spray device with a concealed electric conductive structure of the present utility model, the wire on the bracket has a concealed configuration; in addition, the conductive pivoting structure is electrically connected to the control means. In this way, no wire is exposed between the bracket and the control means. Hence, the present utility model achieves a simple configuration and can prevent the wire from being torn off. In addition, by virtue of the conductive pivoting structure, the present utility model can control the operation of the vibrator via the control means; also the bracket can be more easily pivoted with the control means.

DETAILED DESCRIPTION

The structural features and other functions and objects of the present utility model will be further described in detail in reference to the accompanying drawings.

Figure 1:
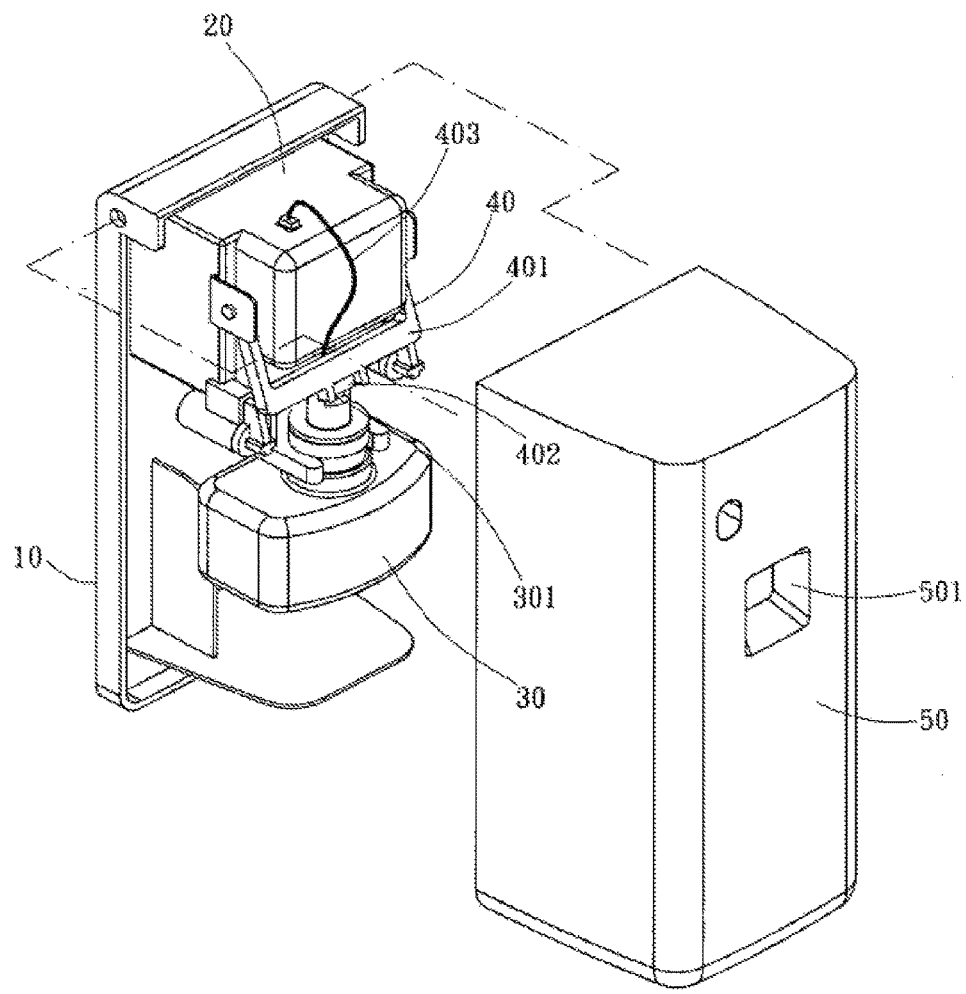
FIG. 1 is a perspective schematic view of the wire connection of a conventional liquid spray device.
Figure 2:
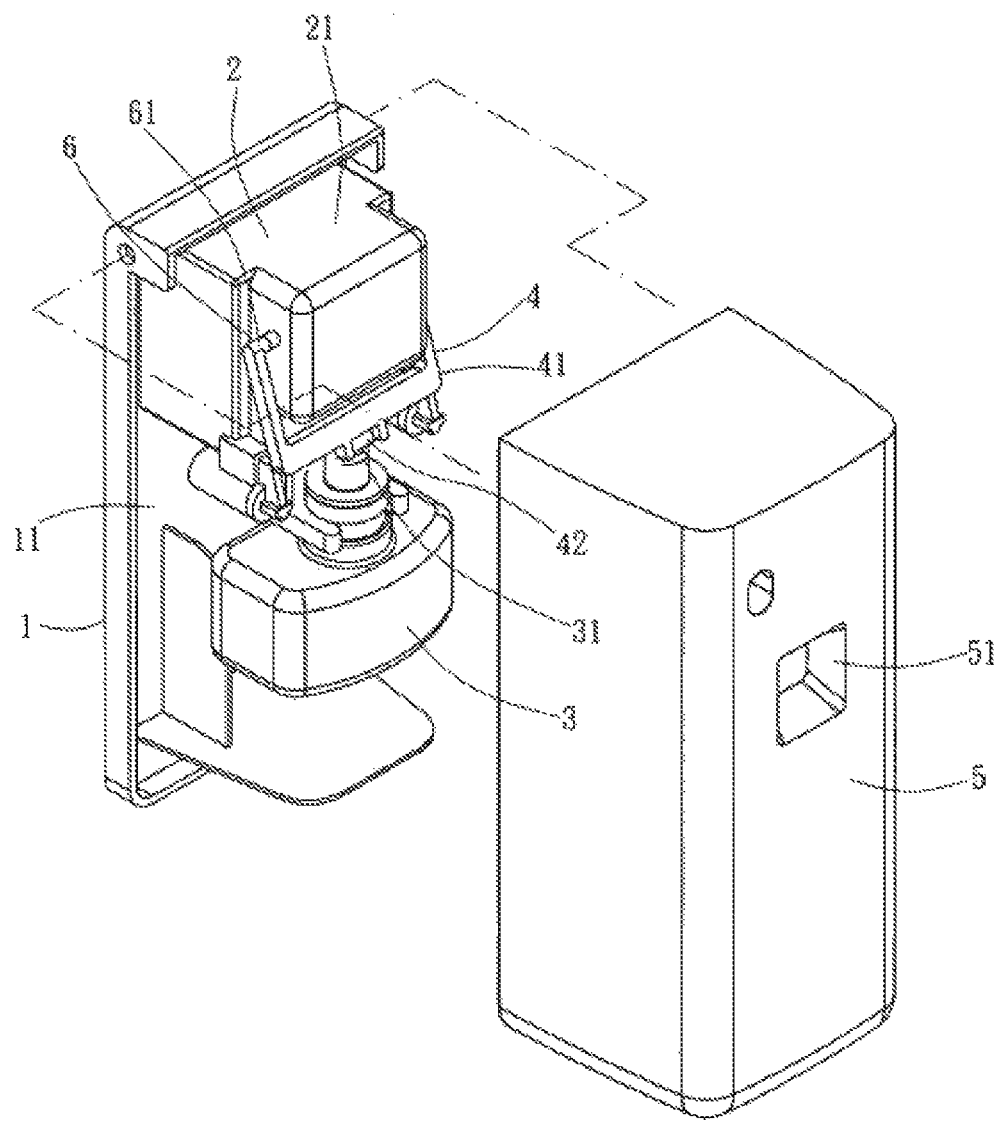
FIG. 2 is a perspective schematic view of the liquid spray device of the present utility model when the bracket is in a combined state.
Figure 3:
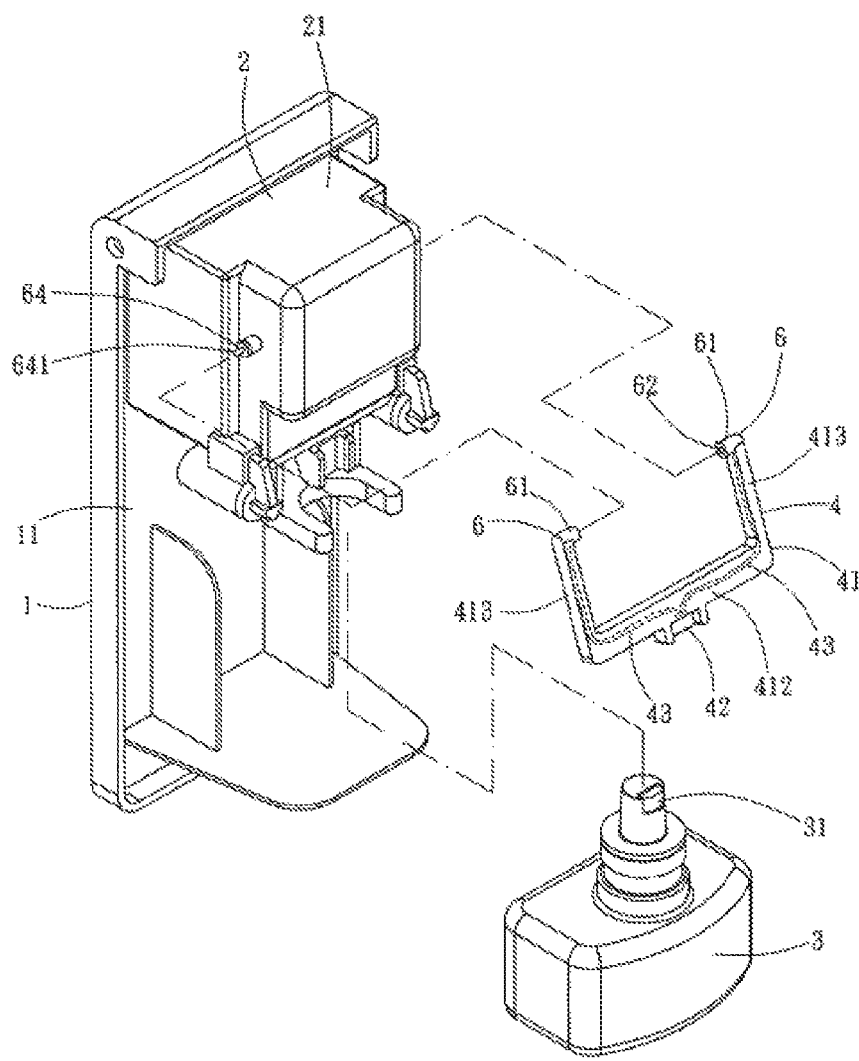
FIG. 3 is a perspective schematic view of the liquid spray device of the present utility model when the bracket is in a separate state.

In reference to FIGS. 2 and 3, the present utility model provides a liquid spray device with a concealed electric conductive structure, which is a liquid spray device for atomizing and then spraying a liquid, in particular a wall mounted liquid spray device that is used for atomize and then spray an air refresher. A preferred embodiment of the present utility model comprises: a base 1, a control means 2, a liquid storage means 3, a spray unit 4, and a housing 5, wherein the base 1 is used for vertically mounted the device on a wall or vertically placed the device on a foundation. The base has a front side 11 for accommodating the control means 2, the liquid storage means 3, the spray unit 4, and the housing 5. The control means 2 is arranged on the front side 11 of the base 1, which has a case 21 and a power source unit and a control unit, and the like (not shown) arranged within the case 21. The control means 2 is used for setting and controlling the operation, stop and intermittent operation of the spray unit 4. The liquid storage means 3 is separately arranged above or below the control means. It is used for store an air refresher or other type of liquid. One end of the liquid storage means is provided with a liquid sucking outlet 31. Preferably, the spray unit 4 comprises a bracket 41, a vibrator 42 arranged on the bracket 41, the bracket 41 is movably connected to two sides of the control means 2 or another location. The vibrator 42 abuts against the liquid sucking outlet 31 of the liquid storage means 3 via the movement of the bracket 41. The housing 5 is separately connected to the front side 11 of the base 1, for example, the upper end of lower end of the housing 5 is pivoted with the base 1, which allows the housing 5 to open via flipping and close via flipping back, so as to cover the control means 2, the liquid storage means 3, and the spray unit 4. Moreover, a spray opening 51 is provided at a location corresponding to the vibrator 42.

Figure 4:
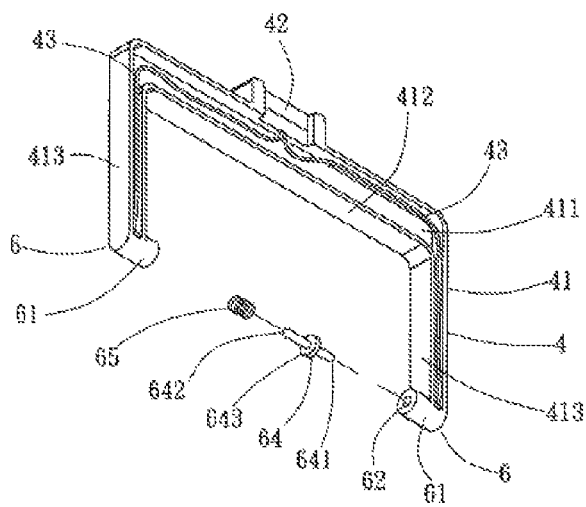
FIG. 4 is an exploded schematic view of the partial structure of the separated conductive pivoting structure of the present utility model.
Figure 5:
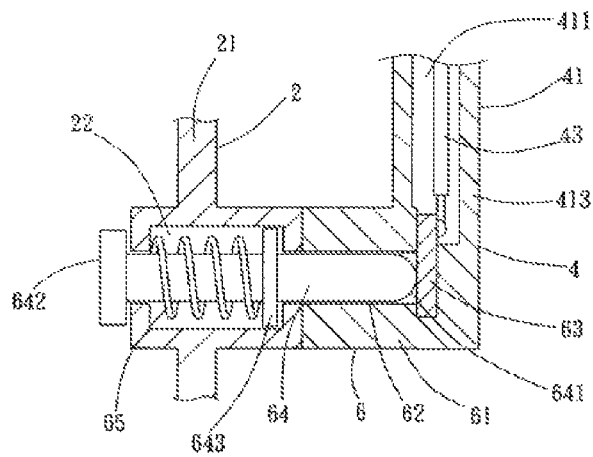
FIG. 5 is a sectional schematic view of the partial structure of the combined conductive pivoting structure of the present utility model.

Further in reference to FIGS. 3, 4 and 5, as an improvement provided in the present utility model, a conductive pivoting structure 6 is provided between the control means 2 and the bracket 41, the bracket 41 is provided with a wire recess 411, and a wire 43 is arranged within the wire recess 411, one end of the wire 43 is electrically connected to the conductive pivoting structure 6, and the other end of the wire 43 is electrically connected to the vibrator 42. In this way, the wire 43 is hidden in the bracket 41. It is electrically connected to the control means 2 via the conductive pivoting structure 6. Further, as shown in FIGS. 4 and 5, the conductive pivoting structure 6, in one preferred embodiment, comprises a pivoting part 61 provided on one side or two sides of the bracket 41, the pivoting part 61 comprises a pivot hole 62, a conductive element 63 is provided in the pivot hole 62. In this way, one end of the wire 43 is electrically connected to the conductive element 63; the other end of the wire 43 is electrically connected to the vibrator 42. In addition, one rod shaped metal terminal 64 is provided on one side or two sides of the control means 2, one outer end 641 of the metal terminal 64 extends into the pivot hole 62 of the pivoting part 61 on the bracket 41, the outer end 641 of the metal terminal 64 contacts the conductive element 63, and one inner end 642 of the metal terminal 64 extends into the case 21 of the control means 2, and conductively connects to a control unit in the control means 2. As a result, the wire 43 is electrically connected to the control unit in the control means 2 via the conductive element 63 and the metal terminal 64. In addition, the bracket 41 is able to achieve the movable pivoting configuration via the metal terminal 64. Such that the liquid spray device with a concealed electric conductive structure according to the present utility model can be achieved.

Further referring FIGS. 4 and 5, the bracket 41, in one preferred embodiment, comprises a cross bar 412 and two vertical bars 413 connected to two ends of the cross bar 412, one sides of the cross bar 412 and the vertical bars 413 are provided with the wire recess 411, the vibrator 42 is arranged in the center of the cross bar 412, and the pivoting part 61 of the conductive pivoting structure 6 is arranged on one end of the vertical bar 413. The conductive element 63 of the conductive pivoting structure 6 is a metal sheet arranged in the pivot hole 62. The conductive element 63 is a conductive medium between the wire 43 and the metal terminal 64. Moreover, the metal terminal 64 is a cylinder, and the metal terminal 64 is movably arranged to pass through one side or two sides of the case 21 of the control means 2. Furthermore, the conductive pivoting structure 6 may further comprises an elastic element 65, one end of the elastic element 65 abuts against the metal terminal 64, and the other end of the elastic element 65 abuts against the case 21 of the control means 2. In this way, the metal terminal 64 is able to retract back to the case 21 and then extends to move back to the original position. The foregoing design can facilitate the device assembly by enabling the pivot hole 62 of the pivoting part 61 aligns with the metal terminal 64. At the same time, by virtue of the elasticity of the elastic element 65, the metal terminal 64 can stably contact the conductive element 63.

Further referring FIGS. 3 and 5, one side or two sides of the case 21 of the control means 2 is provided with an accommodating hole 22, the metal terminal 64 is movably arranged to pass through the accommodating hole 22. In addition, the elastic element 65 is a spiral spring set outside of the metal terminal 64, one end of the spiral spring abuts against a convex ring portion 643 of the metal terminal 64, and the other end of the spiral spring abuts in the bottom of the accommodating hole 22. In this way, driven by the elasticity of the spiral spring, the outer end 641 of the metal terminal protrudes from the accommodating hole 22, so as to insert into the pivot hole 62 of the pivoting part 61 on the bracket 41, and further connect with the conductive element 63 within the pivot hole 62.

When in use, a liquid storage means 3 can be loaded into the liquid spray device of the present utility model. The liquid storage means is arranged in a certain location 23 above or below the control means 2 in a vertical or inverted position, such that the liquid sucking outlet 31 of the liquid storage means 3 corresponds to the vibrator 42. When the vibrator 42 moves close to the liquid sucking outlet 31 via the bracket 41, the control means 2 is able to control the atomization of the liquid based on the ultrasonic vibration mechanism; and the atomized liquid can be further sprayed from the spraying opening 51 on the front side of the housing 5. Accordingly, the present utility model is especially suitable for atomizing and then spraying an air refresher. Moreover, when the liquid stored in the liquid storage means 3 runs out, the housing 5 can be opened for replacing a new liquid storage means 3. In this case, when a user opens the housing 5, since the wire 43 is completely concealed, the present utility model can prevent the wire from being touched or torn off. In addition, the concealed wire 43 can provide a desirable internal space.

In summary, the liquid spray device with concealed electric conductive structure of the present utility model possesses utility and inventiveness, and the technical means employed are also novel. In addition, the function and effect thereof are in line with the objects of the present utility model. Therefore, an application for utility model patent is filed to the Patent Office for examination.

What is claimed is:

1. A liquid spray device with a concealed electric conductive structure, which is used for atomizing and then spraying a liquid stored therein, comprising:
    a base;
    a control means arranged on a front side of the base;
    a liquid storage means separately arranged above or below the control means, and provided with a liquid sucking outlet;
    a spray unit comprising a bracket and a vibrator arranged on the bracket, wherein the bracket is movably pivoted on the control means, and the vibrator abuts against the liquid sucking outlet of the liquid storage means via the movement of the bracket; and
    a housing separately connected to the base to cover the control means and the spray unit, wherein a spray opening is provided at a location corresponding to the vibrator, and wherein a conductive pivoting structure is provided between the control means and the bracket, the bracket is provided with a wire recess, a wire is arranged within the wire recess, one end of the wire is electrically connected to the conductive pivoting structure, and the other end of the wire is electrically connected to the vibrator.

2. The liquid spray device with a concealed electric conductive structure according to claim 1, wherein the conductive pivoting structure comprises a pivoting part provided on the bracket, the pivoting part comprises a pivot hole, a conductive element is provided in the pivot hole, one end of the wire is electrically connected to the conductive element, the other end of the wire is electrically connected to the vibrator, one rod shaped metal terminal is provided on one side of the control means, one outer end of the metal terminal extends into the pivot hole of the pivoting part on the bracket, the outer end of the metal terminal contacts the conductive element, and one inner end of the metal terminal extends into the control means and conductively connects to a control unit in the control means.

3. The liquid spray device with a concealed electric conductive structure according to claim 2, wherein the bracket comprises a cross bar and two vertical bars connected to two ends of the cross bar, one side of the cross bar and one side of each of the two vertical bars are provided with the wire recess, the vibrator is arranged on the cross bar, and the pivoting part is arranged on one end of each of the two vertical bars.

4. The liquid spray device with a concealed electric conductive structure according to claim 2, wherein the conductive element is a metal sheet.

5. The liquid spray device with a concealed electric conductive structure according to claim 2, wherein the metal terminal is a cylinder, and the metal terminal is movably arranged to pass through one side of the control means.

6. The liquid spray device with a concealed electric conductive structure according to claim 5, wherein the conductive pivoting structure further comprises an elastic element, one end of the elastic element abuts against the metal terminal, and the other end of the elastic element abuts against the control means.

7. The liquid spray device with a concealed electric conductive structure according to claim 6, wherein the control means comprises a case, one side of the case is provided with an accommodating hole, the metal terminal is movably arranged to pass through the accommodating hole, the elastic element is a spiral spring set outside of the metal terminal, one end of the spiral spring abuts against a convex ring portion of the metal terminal, and the other end of the spiral spring abuts in the accommodating hole.

8. The liquid spray device with a concealed electric conductive structure according to claim 7, wherein the outer end of the metal terminal protrudes from the accommodating hole.

* * * * *